United States Patent [19]
Kussendrager et al.

[11] Patent Number: 5,596,082
[45] Date of Patent: Jan. 21, 1997

[54] PROCESS FOR ISOLATING LACTOFERRIN AND LACTOPEROXIDASE FROM MILK AND MILK PRODUCTS, AND PRODUCTS OBTAINED BY SUCH PROCESS

[75] Inventors: Klaas D. Kussendrager, Veghel; Marinus G. C. Kivits, Schijndel; Albert B. Verver, Uden, all of Netherlands

[73] Assignee: Campina Melkunie BV, Netherlands

[21] Appl. No.: 256,473

[22] PCT Filed: Jan. 14, 1993

[86] PCT No.: PCT/NL93/00014
§ 371 Date: Sep. 20, 1994
§ 102(e) Date: Sep. 20, 1994

[87] PCT Pub. No.: WO93/13676
PCT Pub. Date: Jul. 22, 1993

[30] Foreign Application Priority Data

Jan. 15, 1992 [NL] Netherlands .......................... 9200064

[51] Int. Cl.⁶ ........................................................ A23J 1/20
[52] U.S. Cl. .......................... 530/416; 530/366; 530/380; 530/832; 530/833; 435/192; 426/657
[58] Field of Search ............................ 530/366, 395, 530/400, 412, 416, 380, 832, 833; 435/192

[56] References Cited

U.S. PATENT DOCUMENTS

| | | | |
|---|---|---|---|
| 4,436,658 | 3/1984 | Peyrouset et al. | 530/387.1 |
| 4,667,018 | 5/1987 | Prieels et al. | 530/417 |
| 4,791,193 | 12/1988 | Okonogi et al. | 530/416 |
| 5,087,369 | 2/1992 | Tanimoto et al. | 210/635 |
| 5,179,197 | 1/1993 | Uchida et al. | 530/366 |
| 5,516,675 | 5/1996 | Uchida et al. | 435/192 |

FOREIGN PATENT DOCUMENTS

| | | |
|---|---|---|
| 0253395 | 1/1988 | European Pat. Off. . |
| 0284525 | 9/1988 | European Pat. Off. . |
| 0418704 | 3/1991 | European Pat. Off. . |
| WO89/04608 | 6/1989 | WIPO . |

*Primary Examiner*—Ponnathapura Achutamurthy
*Attorney, Agent, or Firm*—DeWitt Ross & Stevens SC

[57] ABSTRACT

A process for isolating the metalloprotein lactoferrin and the enzyme lactoperoxidase from milk and milk products on an industrial scale is disclosed. The process includes the steps of adsorbing these proteins to a cation exchanger by passing milk or the milk derivatives over the cation exchanger at a high superficial velocity (more than 500 cm per hour) and at a high liquid load (100–600 bed volumes per hour); eluting these proteins, separately or simultaneously, by elution with one or more salt solutions, so as to form one or more eluates; and optionally followed by drying of the eluates.

15 Claims, 3 Drawing Sheets

PROCESS FOR ISOLATING LACTOFERRIN AND LACTOPEROXIDASE FROM MILK AND MILK PRODUCTS, AND PRODUCTS OBTAINED BY SUCH PROCESS

FIELD OF THE INVENTION

The present invention relates to a process for isolating the metalloprotein lactoferrin and the enzyme lactoperoxidase from milk and milk products on an industrial scale.

BACKGROUND OF THE INVENTION

Lactoferrin (LF), a metalloprotein, occurs in minor amounts in milk from mammals. It is capable of binding two molecules of iron per molecule of protein. It thus provides the young mammal with iron in assimilable form. It also functions as a bacteria-inhibiting agent for pathogenic microorganisms that are iron-dependent.

The enzyme lactoperoxidase (LP) catalyzes the breakdown of hydrogen peroxide in the presence of a hydrogen donor or an oxidizable substance. In milk, it functions as a bacteria inhibitor of pathogenic Streptococci and Salmonella in the presence of thiocyanate and peroxide, both of which are present in milk. In raw cow milk, concentrations of about 200 mg/l have been reported for LF and concentrations of about 30 mg/l for LP depending in part on the stage of lactation and breed.

LP in particular is thermolabile. Upon pasteurization, this enzyme will be inactivated in part or in whole, depending on the intensity of the heat treatment. It is therefore typically necessary to isolate these two components from raw milk. However, this may be technologically difficult because small amounts of LP and LF must be separated from large amounts of other substances, e.g., proteins, sugars and fats.

Further, it is not known whether the milk from which LP or LF has been withdrawn can still be used as "milk" in terms of the official food regulations, i.e., for human consumption and/or as raw material for making cheese and butter. It is therefore desirable to avoid using raw milk as the starting product, and instead, use a by-product such as those formed in cheese or butter making, e.g., whey or skim milk.

In cheese making, the milk is subjected only to a minor heat treatment. As a consequence, substantially all of the LP is still present in cheese whey. However, only a part of the LF, namely about 25%, remains. Nevertheless, whey is an attractive starting material. It is available in large amounts; it is cheap; and, in a manner of speaking, it is prepurified.

Reference NL-A 8201947 (U.S. Pat. No. 4,436,658) discloses a process for isolating LP and LF from cheese whey. Whey having a pH between 7.5 and 8.2 is applied to a column filled with buffered silica gel. The proteins adsorbed to the column can be eluted to obtain a LF and a LP. The purity of the preparations obtained is low, e.g., only 66%.

EP-A 0 253 395 discloses the isolation of LF alone from raw milk and whey. Milk or whey is brought in contact with a weakly-acid ion exchanger with carboxymethyl groups as active groups. Various types of exchangers were compared and characterized by a binding capacity for hemoglobin. The examples describe long contact and elution times. The experiments were performed both in columns and in batches. This implies that the process described in EP-A 0 253 395 is less suitable for large-scale industrial production. Moreover, only LF is isolated, while LP is not.

EP-A 418 704 discloses the extraction of LP and LF via affinity chromatography in a column with sulfonated polysaccharide resin. LP and LF are adsorbed and subsequently eluted and purified. In the examples described, a small liquid load is used (about 80 bed volumes per hour), yielding good separation of LP and LF.

WO-A 89/04608 discloses a process whereby LP and LF can be isolated from cheese whey on a semi-industrial scale. Here, too, the rate of throughput of 1–1.5 bed volume per minute is a limiting factor, in view of the large volumes of cheese whey that must be passed through the columns.

The above-mentioned processes are based on known chromatographic techniques for the extraction and purification of proteins from a matrix containing many attendant substances, such as carbohydrates, fats and salts. The above-mentioned techniques are used in particular on a laboratory scale and also on a semi-industrial scale.

The resin and ion exchangers that are typically used in these techniques are characterized in particular by a selective binding of the desired protein/protein fractions, optimum binding capacity, and the best possible yield. This implies that very fine particles (about 100 μm) are used, which enable optimum operation in terms of selectivity, binding capacity and yield.

A disadvantage of fine-grained column packings is their high flow resistance. This implies that only low superficial velocities can be used (for instance, up to 500 cm per hour). This does not present a problem in analytical and/or preparatory processes for isolating proteins, particularly if the concentration of the starting materials is sufficiently high. When the concentrations are very low, as with LF and LP in whey, large quantities of the liquid must be passed through the columns.

If the superficial velocity is increased, the pressure on the column and the column material will increase. The maximum pressure the ion exchanger itself is capable of resisting limits the superficial velocity. The pressure, or more realistically, the pressure drop, is usually expressed in bar per meter bed height. Accordingly, the bed height becomes the limiting factor. This implies that the diameter of the column must be chosen to be large if large amounts of liquid are to be processed per unit time (high flow rates). This requires the construction of the column to meet extremely high standards in order to provide the required mechanical robustness and adequate distribution of the liquid. This has consequences for the economy of the process, on the one hand on account of the cost of such columns, and, on the other hand, on account of the high cost of the resin.

SUMMARY OF THE INVENTION

A process has now been found which makes it possible to isolate the bio-active proteins LP and LF from milk or a milk derivative on an industrial scale by:

a) adsorbing these proteins to a cation exchanger by passing the milk or the milk derivative over the cation exchanger at a high superficial velocity (more than 500 cm per hour) and at a high liquid load (100–600 bed volumes per hour);

b) eluting these proteins, separately or simultaneously, by elution with one or more salt solutions, so as to form one or more eluates; and optionally followed by c) drying of the eluates.

DETAILED DESCRIPTION OF THE INVENTION

Figure 1:
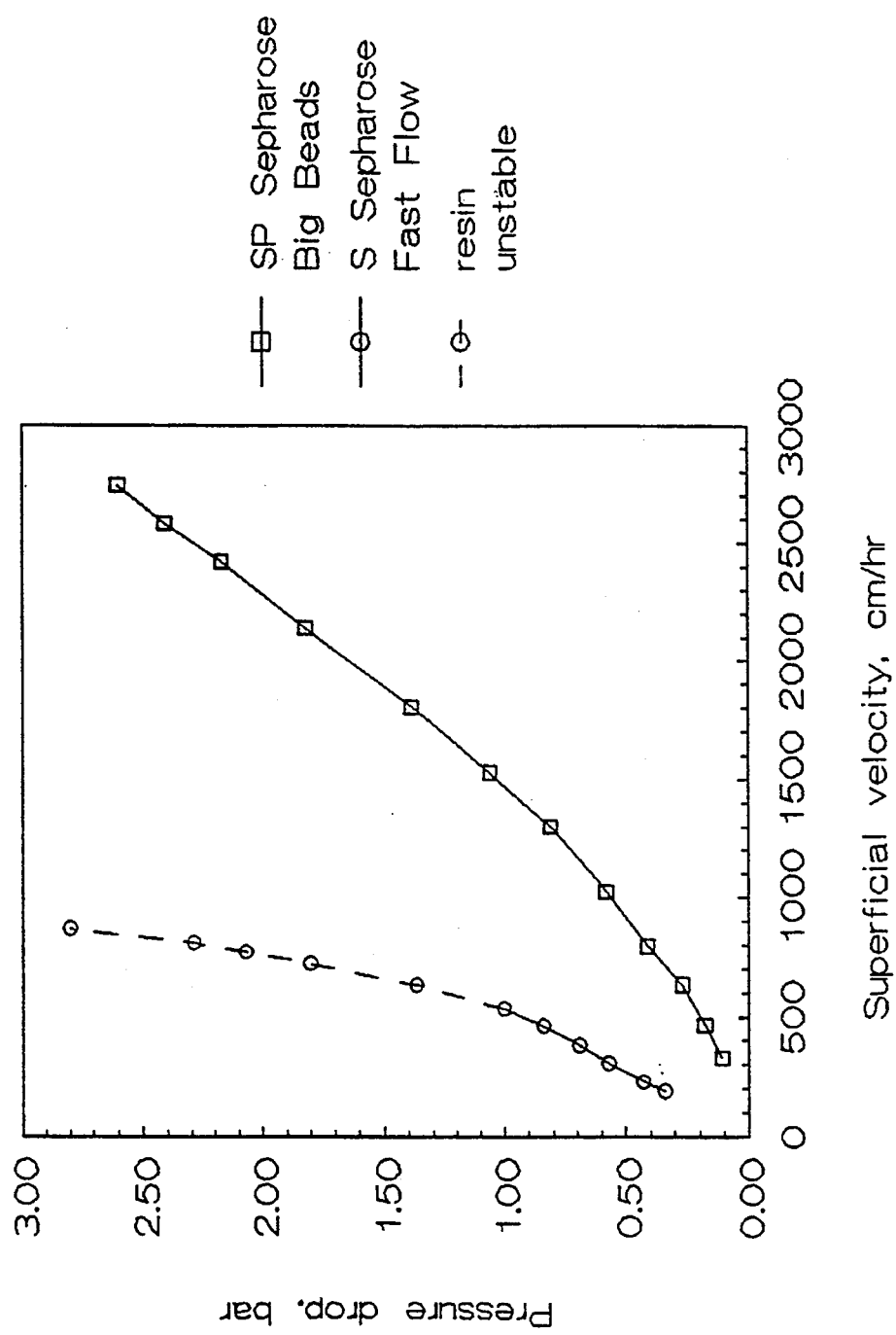
FIG. 1 is a graph illustrating the plot of the pressure drop (delta P) across the column bed as a function of the superficial velocity in Example 2.

In the preferred embodiment, the starting material is cheese whey (obtained in cheese making) or neutralized casein whey (pH 6.5) obtained from skim milk (after casein precipitation). Advantageously, the heat treatment in the preceding processes is so mild that sufficient amounts of LP and LF are still present.

Cheese whey which has been obtained in the conventional manner in cheese making is suitable. Because the process as a whole takes a relatively long time and the cheese whey contains microorganisms as a result of the cheese preparation, it is recommended to reduce the number of microorganisms in this phase. For the reasons mentioned above, conventional heat pasteurization cannot be considered. Suitable methods include bactofugation, ultrafiltration over a coarse filter or microfiltration.

An additional advantage involved here is that coarse contaminants and protein- and fat-agglomerates are removed at the same time. The whey is subsequently passed at a high velocity over a coarse-grained ion exchanger which also comprises a large number of functional groups.

The cation exchanger used in accordance with the present invention preferably has a mean (number) particle diameter of at least 100 µm, preferably at least 125 µm, and more preferably at least 150 µm. The upper limit for the particle diameter is preferably 300 µm as higher diameters are not expected to provide additional advantages. Use of such particle sizes provides the possibility to have high superficial velocities in the adsorption.

Additionally, it is preferred that the cation exchanger has such a high physico-mechanical stability that a pressure drop exceeding the usual values of 10 bar/m bed height, such as 40 bar/m bed height, can be applied.

It was found that an exchanger such as the SP Sepharose Big Beads (Pharmacia) meets these criteria and accordingly functions well.

The mechanical stability of such an ion exchanger allows a pressure drop of at least 40 bar/m bed height. The use of a working pressure of up to 3 bar/10 cm bed height resulted in superficial velocities of 3,000 cm/hour, and rates of throughput of up to 600 bed volumes per hour. In a preferred embodiment the cation exchanger is present as an adsorption bed in a column, the superficial velocity of the milk and/or milk derivatives being 2,000–3,000 cm per hour and a liquid load of 100 to 300 bed volumes per hour.

In addition to a high rate of flow, the economy of the process is also determined by the binding capacity and binding rate of the resin. It has now been found that the resin used could be charged to, respectively, about 60 g LF and 30 g LP per liter of resin. This implies that the active groups of the resin, even at such high rates of flow, are utilized substantially completely.

It was also found that, even at the high rate involved, the LP and LF were substantially completely adsorbed to the column. Only when the above-mentioned binding capacity has been closely reached, more leakage occurs (more than 20%). According to a preferred embodiment the binding capacity of the ion exchanger is more than 10 g LP and more than 10 g LF per liter bed volume and more than 80% of the said proteins is extracted.

The ion exchanger is preferably first conditioned with a phosphate buffer of pH 6.5 (0.025 mol $Na_2HPO_4$/$NaH_2PO_4$). A throughput of about 4 bed volumes of buffer is sufficient to equilibrate the column. After charging the column with clarified cheese whey, the column is first rinsed with buffer to displace the last cheese whey residues. The LF and LP can be eluted from the column either separately or simultaneously.

If elution is effected with a concentrated buffered salt solution (>0.7 molar NaCl), LP and LF are eluted simultaneously. Elution with a low salt concentration (about 0.2–0.5 molar NaCl) only yields LP. A subsequent elution with a higher salt concentration (up to 2.5 molar NaCl) then yields only LF. In this way, these two bio-active proteins can be eluted separately.

These eluates are not suitable to be used as such, because the salt concentration is too high. For desalting, the conventional techniques such as ion exchange, electrodialysis, and ultrafiltration/diafiltration are eligible. The last-mentioned technique is preferred because in that manner any desired residual salt concentration can be readily set.

The LP and LF fractions, unsalted or not, can subsequently be dried. Conventional drying techniques such as spray-drying, vacuum-drying, roller-drying and freeze-drying can be used. In view of the thermolability of these bio-active proteins, freeze-drying is the most important and preferred option among them, but the other techniques are certainly eligible as well, if the proper precautions with regard to the heat load are taken.

EXAMPLES

The invention is further explained and illustrated in and by the following non-limiting examples.

Example 1

An ion exchange chromatography column having a diameter of 1.6 cm was packed with 20 ml of the strong cation exchanger S Sepharose Big Beads (Pharmacia). The bed height was 10 cm. Clarified cheese whey, obtained by cross-flow microfiltration 1.4 µm (Alfa Laval), having a solids content of 5.6% and a pH of 6.6, was pumped through the column at different superficial velocities (cm/hour) at room temperature, until conditions were stable (about 10 minutes). The pressure drop (delta P) across the bed of the ion exchanger in the column was measured as a function of the superficial velocity. A similar series of experiments were carried out with the same column packed with the strong cation exchanger S-Sepharose Fast Flow (Pharmacia).

It was found that at pressure differences in excess of about 1.5 bar, the S Sepharose Fast Flow column bed was increasingly compressed. The loss of porosity as a result of this physicomechanical instability gave rise to a further increase of the pressure drop, which rendered this resin unsuitable for use. The supplier of this resin specifies a liquid velocity of up to 400 cm/hour at a pressure drop of 1 bar/15 cm. The measuring results are summarized in the following table:

| Superficial Velocity Cheese Whey | | Presure Drop Across the Column Bed in Bar | |
|---|---|---|---|
| In CM/ Hour | Bed Volumes/Hour | S Sepharose BB | S Sepharose FF |
| 600 | 60 | <0.1 | 0.5 |
| 900 | 90 | 0.25 | 1.2 |
| 1,200 | 120 | 0.5 | 2.0* |
| 1,800 | 180 | 1.2 | 7.0* |
| 2,400 | 240 | 1.9 | — |
| 3,000 | 300 | 2.5 | — |
| 3,600 | 360 | 3.2 | — |
| 4,500 | 450 | 4.0 | — |

*stable conditions not possible

The S Sepharose BB column keeps its physical and mechanical stability and thus its excellent performance characteristics to a pressure drop of at least 4 bar/10 cm bed height. This means that the column can resist a superficial velocity of at least 4500 cm/h.

Example 2

Example 2 was conducted to determine whether the data from Example 1 also apply on a larger scale.

A column of a pilot chromatography system, with a diameter of 10 cm, was packed with the ion exchanger SP Sepharose Big Beads. The bed height was 11 cm and the bed volume was 0.864 l. Clarified cheese whey having a solids content of 5.6 and a pH of 6.6 was pumped through the column at different superficial velocities (cm/hour) at room temperature and the pressure drop across the column bed was measured as a function of the superficial velocity. The superficial velocity was varied within the range of 300 to 2,800 cm/hour, corresponding with 27 to 255 bed volumes/hour.

A similar series of experiments was carried out with the same column filled with the ion exchanger S Sepharose Fast Flow, with variation of the superficial velocity within the range of 200 to 880 cm/hour, corresponding with 18 to 80 bed volumes/hour.

The measured results are shown in the graph of FIG. 1, where the pressure drop (delta P) across the column bed is plotted as a function of the superficial velocity. It appeared that at a pressure drop in excess of 1.5 bar, the S Sepharose Fast Flow column bed was appreciably compressed. It was further established that at a set pressure drop from about 1 bar, the superficial velocity decreases over time, so that, after some time, the column became unsuitable for continuous use.

The column packed with SP Sepharose Big Beads maintains its good through-flow properties and physical stability at least up to the maximum superficial velocity and pressure drop applied.

FIG. 1 shows inter alia that, at a pressure drop of 1 bar, the superficial velocity (and hence the number of bed volumes/hour) is about three times higher with the SP Sepharose Big Beads than with the S Sepharose Fast Flow. Moreover, when the SP Sepharose Big Beads column is used, a much higher pressure drop can be realized, so that the advantage as to the superficial velocity (cm/hour) or bed volumes/hour relative to the S Sepharose Fast Flow column is even considerably higher still, for instance by a factor of 5 or 6 at a pressure drop of 2.5 bar across the column bed of SP Sepharose Big Beads.

Figure 2:
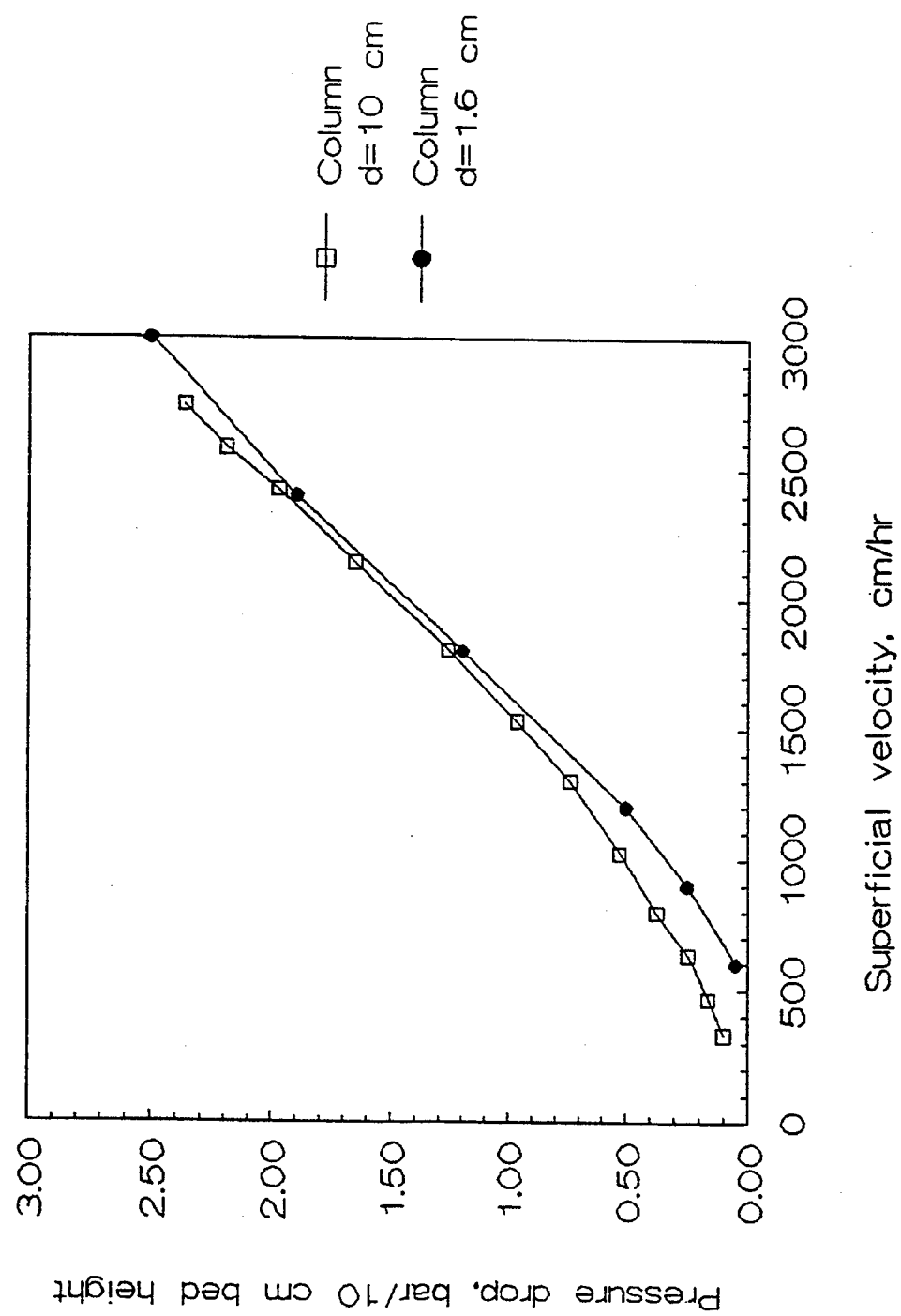
FIG. 2 is a graph illustrating the results of the SP Sepharose Big Beads column in Example 2 as compared with the results in Example 1.

In the graph of FIG. 2, the results of the SP Sepharose Big Beads column are compared with those of Example 1.

Example 3

The particular economic and technological advantages of the column-process for the selective adsorption of LP and LF according to the invention, in particular with respect to dimensioning and use on an industrial scale, are illustrated by a comparison of situations with a conventional cation exchanger on the one hand and an improved type of cation exchanger with reduced flow resistance on the other.

As an example of dimensioning on an industrial scale, the starting point is a cheese whey load on the column of 20 $m_3$/hour, being the output of a Dutch cheese factory of typical size.

Conditions for the comparison:

Conventional cation exchanger: S-Sepharose Fast Flow. The pressure drop across a packed column when charged with cheese whey is maximally about 6.7 bar/m bed height, at a superficial velocity of maximally 400 cm/hour.

Improved cation exchanger: S-Sepharose Big Beads. The pressure drop across a packed column when charged with cheese whey is about 25 bar/m bed height at a superficial velocity of 3,000 cm/hour.

The results of the comparison are summarized in the following table, wherein:

B=bed volumes of cheese whey per hour.

KV=volume of the column bed in liters.

h=column bed height in m.

d=column bed diameter in m.

| B | KV | S-Sepharose Fast Flow h | d | S-Sepharose Big Beads h | d |
|---|---|---|---|---|---|
| 60 | 333 | 0.067 | 2.52* | 0.5 | 0.92 |
| 90 | 222 | 0.044 | 2.52* | 0.33 | 0.92 |
| 150 | 133 | 0.027 | 2.52 | 0.20 | 0.92 |
| 200 | 100 | 0.020 | 2.52 | 0.15 | 0.92* |
| 300 | 67 | 0.013 | 2.52 | 0.10 | 0.92* |
| 450 | 44 | 0.009 | 2.52 | 0.067 | 0.92 |

*Optimum working conditions

This table clearly shows that the exceptionally high superficial velocity in the case of the new type of resin offers major advantages with respect to the permissible dimensions of the columns (diameter, bed height) and with respect to the permissible cheese whey loads on the columns (important parameters for the economy of the process).

Example 4

This example was set up to determine the binding capacity and the yield.

A column having a diameter of 1.6 cm was packed with 20 ml S Sepharose Big Beads ion exchanger. The bed height was 10 cm. After equilibration of the resin with 0.025M phosphate buffer pH 6.5, clarified cheese whey was pumped through the column at a rate of 150 bed volumes/hour in the first test and at a rate of 200 bed volumes/hour in the second test. The cheese whey contained, respectively, 36 and 40 mg/l LF and, respectively, 17 and 19 mg/l LP. The total throughput of cheese whey was 34 l (about 1,700 bed volumes) in the first test and 20 l (about 1,000 bed volumes) in the second test.

After washing of the column with buffer, LP and LF were separately eluted in the conventional manner with, respectively, 0.3M NaCl in phosphate buffer and 0.8M NaCl in phosphate buffer. The eluates obtained were analyzed for LP and LF content by means of HPLC. The results are summarized in the following table:

| | Test 1 (150 Bed Volumes/Hour) | | Test 2 (200 Bed Volumes/Hour) | |
|---|---|---|---|---|
| | LP | LF | LP | LF |
| Bound Amt. g/l resin | 27 | 57 | 15 | 36 |
| Yield % From the Whey | 85 | 94 | 89 | 91 |

Example 5

A 10 cm column of a pilot production chromatography system (Bioprocess System Pharmacia) was packed with SP Sepharose Big Beads ion exchanger. The diameter of the column was 10 cm, the bed height was 11 cm and the bed volume was 0.864 l.

After equilibration of the resin at room temperature with 0.025M phosphate buffer pH 6.5, clarified cheese whey was pumped through the column for 3 hours and 35 minutes at a rate of flow of 180 liter/hour. The superficial velocity was 2,300 cm/hour. The liquid load in this case was 208 bed volumes/hour. The total throughput of cheese whey was 650 l.

Figure 3:
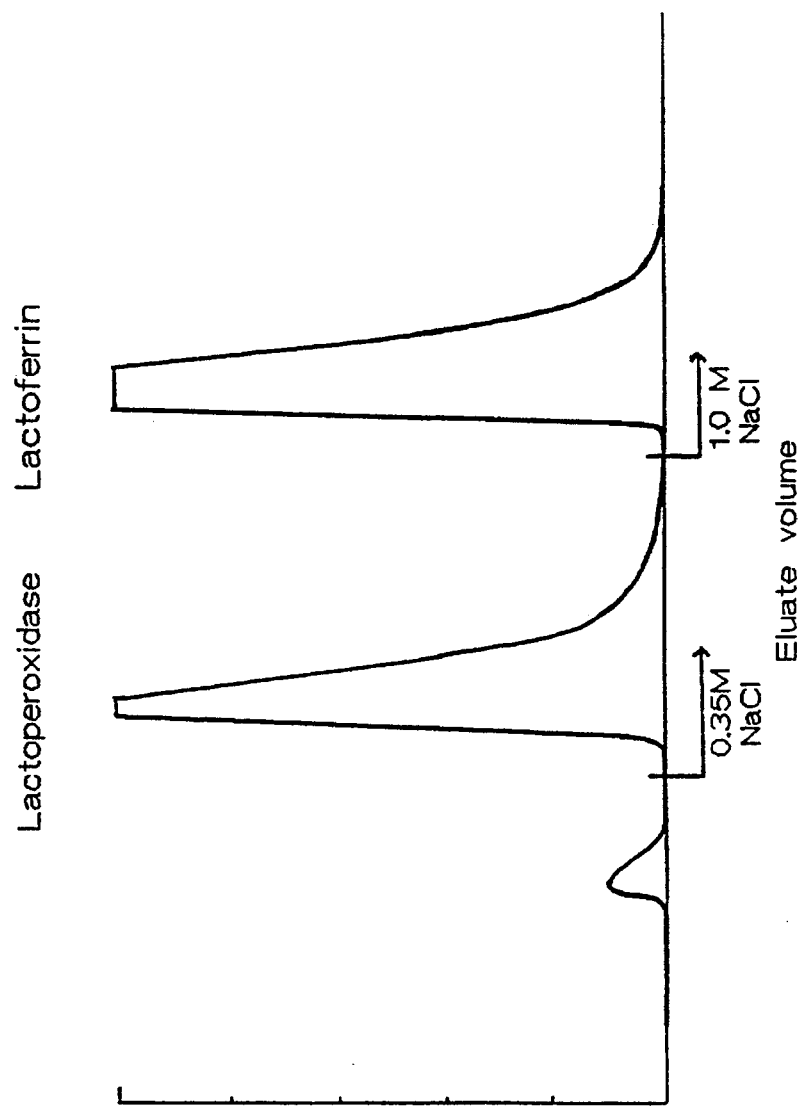
FIG. 3 is a graph illustrating the elution diagram in Example 5.

After washing of the column with buffer solution, LP and LF were separately eluted with, respectively, 0.35M NaCl in phosphate buffer and 1.0M NaCl in phosphate buffer. The liquid flow rate during washing and elution was 8.6 liter/hour (10 bed volumes/hour). FIG. 3 shows the elution diagram.

Thus, 2.8 l LP eluate and 2.2 l LF eluate were obtained. The LP content of the LP fraction was determined by means of the enzymatic method and via HPLC, being 4.6 g/l. The LP yield was 94% relative to the LP in the whey.

The LF of the LF fraction, determined by means of UV absorption (A280) and HPLC, was 9.0 g/l.

The LF yield was 96% relative to the LF in the whey. The LP eluate and the LF eluate were desalted by means of ultrafiltration/diafiltration with the Pellicon system (Millipore) equipped with polysulfone membranes having a cut-off value of 10 kD, and subsequently freeze-dried.

The purities of LP in the LP preparation and LF in the LF preparation, determined by means of HPLC, were 93% and 94%, respectively, calculated on total solids.

These results demonstrate that if this type of ion exchanger is used in columns on a pilot production scale, extremely high superficial velocities of the whey can be applied and that, further, very high yields and purities of the two bio-active proteins are obtained.

Example 6

Analogously to Example 5, a chromatography column having a diameter of 10 cm was packed with SP Sepharose Big Beads ion exchanger to a bed height of 4.8 cm.

The bed volume was 0.377 l.

After equilibration of the ion exchanger as described in Example 5, clarified cheese whey was pumped through the column at a flow rate of 513 bed volumes/hour (193 l/h). The superficial velocity was 2,460 cm/hour. A total amount of 250 l whey was passed through the column.

The LP and LF-charged column was washed and eluted as described in Example 5, with a liquid flow rate of 10 bed volumes/hour.

The obtained eluates with LP and LF, 1.5 l and 1.3 l, respectively, were analyzed for the content of bio-active proteins in the conventional manner. The LP fraction contained a total of 4.70 g LP and the yield 5 from the whey was 82%. The LF fraction contained a total of 6.75 g LF and the yield from the whey was 90%.

What is claimed:

1. A process for isolating lactoperoxidase and lactoferrin from milk or milk derivatives, comprising the following steps:

a) adsorbing the lactoperoxidase and lactoferrin to a cation exchanger having a mean particle diameter of from 100 µm to 300 µm by passing the milk or milk derivatives over the cation exchanger at a superficial velocity of at least about 600 cm per hour and a liquid load between about 100 and 600 bed volumes per hour; and b) eluting the lactoperoxidase and lactoferrin with at least one salt solution to form at least one eluate.

2. The process according to claim 1 wherein the cation exchanger is present as an adsorption bed in a column, wherein the superficial velocity of the milk or milk derivatives is between about 2,000–3,000 cm per hour, and wherein the liquid load is between about 100 and 300 bed volumes per hour.

3. The process according to claim 1 wherein the binding capacity of the ion exchanger is more than 10 g lactoperoxidase and more than 10 g lactoferrin per liter bed volume, and wherein more than 80% of the lactoperoxidase and lactoferrin is extracted.

4. The process according to claim 1 wherein the milk derivative is selected from the group consisting of skim milk, evaporated skim milk, buttermilk, milk protein concentrate, cheese whey, casein whey, whey concentrate, desalted whey, desalted whey concentrate and whey-protein concentrates.

5. The process according to claim 1 further comprising removing the coarser contaminants to clarify the milk derivatives.

6. The process according to claim 1 wherein the lactoperoxidase and lactoferrin are eluted from the columns separately.

7. The process according to claim 1 wherein the lactoperoxidase and lactoferrin are eluted from the column simultaneously.

8. The process according to claim 1 wherein the lactoperoxidase and lactoferrin are eluted from the column with salt solutions having a concentration no greater than about 2.5 moles per liter.

9. The process according to claim 1 wherein the lactoperoxidase and lactoferrin are eluted from the column with salt solutions having a concentration of about 2 moles per liter.

10. The process according to claim 1 further comprising desalting said eluates.

11. The process according to claim 1 further comprising concentrating said eluates.

12. The process according to claim 1 further comprising drying said eluates.

13. The process according to claim 12 wherein said eluates are dried by vacuum-drying, freeze-drying, spray-drying or roller-drying.

14. The process according to claim 1 wherein the milk or milk derivatives are passed over the cation exchanger at a superficial velocity of at least about 900 cm per hour.

15. The process according to claim 1 wherein the milk or milk derivatives are passed over the cation exchanger at a superficial velocity of at least about 1200 cm per hour.

* * * * *